US006528252B2

(12) United States Patent
Chadwick et al.

(10) Patent No.: US 6,528,252 B2
(45) Date of Patent: Mar. 4, 2003

(54) METHODS FOR IDENTIFYING A PROTEASE INHIBITOR

(75) Inventors: Mark P. Chadwick, Cambridge (GB); Stephen J. Russell, Rochester, MN (US)

(73) Assignee: BioFocus Discovery Limited, Cambridge (GB)

( * ) Notice: Subject to any disclaimer, the term of this patent is extended or adjusted under 35 U.S.C. 154(b) by 0 days.

(21) Appl. No.: 09/791,426

(22) Filed: Feb. 23, 2001

(65) Prior Publication Data

US 2002/0072075 A1 Jun. 13, 2002

Related U.S. Application Data

(60) Provisional application No. 60/185,203, filed on Feb. 25, 2000.

(51) Int. Cl.$^7$ .......................... C12Q 1/70; C12Q 1/06; G01N 33/53; C12N 5/00; C12N 5/06

(52) U.S. Cl. .......................... 435/5; 435/7.1; 435/39; 435/325; 435/334; 435/339

(58) Field of Search .......................... 435/5, 7.1, 39, 435/325, 334, 339

(56) References Cited

FOREIGN PATENT DOCUMENTS

GB WO 97/12048 4/1997 ........... C12N/15/86

OTHER PUBLICATIONS

Peng, et al., "A Gene Delivery System Activatable by Disease–Associated Matrix Metalloproteinases", Apr. 10, 1997, Human Gene Therapy 8: 729–738.

International Search Report from related application PCT/US01/05859.

*Primary Examiner*—Hankyel T. Park
(74) *Attorney, Agent, or Firm*—Palmer & Dodge LLP; Kathleen M. Williams

(57) ABSTRACT

Methods are disclosed whereby inhibition of proteolytic activity causes an increase in delivery of a transferable label from a viral display package to a target cell. Assaying for the transferable label in the target cell in the presence of a test substance can identify the test substance as a protease inhibitor. Protease inhibitors so identified are used therapeutically, to treat conditions such as cancer, inflammation, rheumatoid arthritis and other autoimmune diseases, and infections, including AIDS, herpes, and hepatitis.

55 Claims, 11 Drawing Sheets

METHODS FOR IDENTIFYING A PROTEASE INHIBITOR

TECHNICAL FIELD OF THE INVENTION

The invention relates to the identification of protease inhibitors.

BACKGROUND OF THE INVENTION

An undesirable level of protease activity occurs in a variety of conditions, including rheumatoid arthritis and other autoimmune diseases, tumor invasion, inflammation, and diseases caused by infections agents which produce proteases, such as HIV, rhinoviruses, hepatitis viruses, and herpes viruses. Protease inhibitors, particularly specific inhibitors, can be used to treat such conditions.

Thus, there is a need in the art for convenient and rapid methods of identifying protease inhibitors.

SUMMARY OF THE INVENTION

It is an object of the present invention to provide methods for identifying protease inhibitors. This and other objects of the invention are provided by one or more of the embodiments described below.

One embodiment of the invention is a method of screening a test substance for the ability to inhibit a protease having a proteolytic activity. The method encompasses the steps of contacting a target cell comprising a protease having a proteolytic activity with a viral display package in the presence of a test substance, wherein the viral display package comprises (a) a transferable label and (b) a recombinant viral envelope protein comprising in sequential order (i) a receptor-binding polypeptide which binds to a receptor on the surface of the target cell, (ii) a protease cleavage site for the protease expressed by the target cell, and (iii) a fusion-mediating polypeptide, such that proteolytic cleavage of the cleavage site does not permit substantial transfer of the transferable label from the viral display package to the target cell; and detecting the transferable label, if any, in the target cell, wherein detection of transferable label or a greater amount of transferable label in the target cell in the presence of the test substance relative to the absence of the test substance identifies the test substance as a protease inhibitor.

A "protease", also called an endoprotease, is an enzyme which hydrolyzes a peptide bond between a pair of amino acids located in a polypeptide chain. The proteolytic activity of the protease does not permit substantial transfer of the transferable label from the viral display package to the target cell.

The "viral display package" comprises a transferable label and a recombinant viral envelope protein. The "transferable label" is a label whose presence is detectable in the target cell as a result of fusion of the viral display package and the target cell membrane. Thus, if the protease produced by the target cell cleaves the protease cleavage site in the recombinant envelope protein, the virus display package does not transfer label to the target cell. Alternatively, where the protease is inhibited, it is unable to cleave the cleavage site, and the virus display package can infect the target cell and transfer label.

Preferably, the transferable label is a gene encoding a selectable marker or is a reporter gene which encodes a detectable product.

The "sequential order" of components comprising a recombinant viral envelope protein occurs sequentially from the N- to C-terminus.

The "receptor-binding polypeptide" is capable of binding to a cognate receptor on the surface of a target cell, and thereby initiating gene delivery to the target cell. For example, the receptor binding polypeptide is capable of binding to a cognate receptor on a target cell, such as a viral envelope receptor on the surface of the target cell. The receptor-binding polypeptide should minimally include the receptor-binding domain of a protein, i.e., the portion of the protein that retains the ability to bind to the receptor on the cell. Thus, receptor-binding polypeptide (e.g., a displayed polypeptide) may be a receptor-binding domain of a viral envelope protein, such as a 4070A envelope protein or Moloney murine leukemia virus envelope protein, which (a) binds to a cell-surface receptor and (b) initiates gene delivery thereby. The underlying envelope protein (on which the receptor binding polypeptide is displayed) must retain its membrane fusion ability but does not necessarily need to retain its receptor-binding capability.

Certain alterations, such as mutations, deletions, or additions, can be made to the receptor-binding polypeptide which do not significantly affect its functions, as described above (a) and (b). One example of a receptor-binding domain useful in the context of this invention is the binding domain for the Pit-2/Ram-1 receptor of the 4070A virus. Other receptor-binding domains include the CAT-1 receptor-binding domain of the Moloney murine leukemia virus, GALV receptor-binding domain, or any of those from MLV envelope proteins.

The "fusion-mediating polypeptide" may be a fusion-mediating domain of a viral envelope protein or a substantially intact viral envelope protein and can be derived either from the same type of viral envelope protein as the receptor-binding polypeptide or from a different viral envelope protein. Viruses such as murine leukemia viruses (e.g., Moloney murine leukemia virus or 4070A murine leukemia virus) are particularly useful as sources of viral envelope proteins. In another embodiment, the recombinant viral envelope protein is a viral envelope protein of a murine leukemia virus, such as a Moloney murine leukemia virus or a 4070A, in which a protease cleavage site has been inserted between the receptor-binding and the fusion-mediating polypeptides.

The "transferable label," if any, is detected in the target cell. Detection of the transferable label or of a greater amount of transferable label in the target cell in the presence of the test substance relative to the absence of the test substance identifies the test substance as a potential protease inhibitor. The "amount" of label transferred in the presence of an inhibitor is considered a "greater amount" if it is at least 10, 20, 25, 50, 75, 85, 90, 95, 98, 99, or 100%, or at least 3-, 4-, 5-, 6-, 7-, 8-, 9-, or 10-fold greater than the amount of transferable label that is transferred from the viral display package to a target cell in the absence of the protease inhibitor. If no amount of label is transferred in the absence of the protease inhibitor, then any detectable label in the presence of the inhibitor is indicative of inhibition and is a "greater amount."

A "protease cleavage site" according to the invention is a contiguous sequence of amino acids connected by peptide bonds which contains a pair of amino acids which is connected by a peptide bond that is hydrolyzed by a particular protease. Optionally, a protease cleavage site according to the invention includes one or more amino acids on either side of the peptide bond to be hydrolyzed, to which the catalytic site of the protease also binds (Schecter and Berger, *Biochem. Biophys. Res. Commun.* 27, 157–62, 1967). Thus, the protease "cleavage site" also may include a protease recognition site, and both sites may be included within an amino acid linker sequence.

Alternatively, a "plurality" of target cells (i.e. more than one target cell) is contacted with a plurality of viral display packages (i.e. more than one viral display package) in the presence of a test substance. In this case, detection of transferable label in a number of target cells or in a greater number of target cells in the presence of the test substance relative to the absence of the test substance identifies the test substance as a potential protease inhibitor. A "greater number" of target cells in which the transferable label is detected is any number of target cells which is at least 1, 2, 5, 10, 20, 50, or 100 more than the number of target cells in which the transferable label is detected in the absence of a protease inhibitor.

In a specific embodiment, an otherwise intact envelope protein has a protease cleavage site inserted at a position that abrogates the function of the envelope protein when cleaved.

In another embodiment, the invention encompasses an MLV envelope protein which is capable of binding to a target receptor and subsequently causing virus-cell fusion, and containing a heterologous protease cleavage site, such that the normal functions of the envelope protein are not impaired. Upon cleavage at the introduced site by a protease, the envelope protein no longer functions.

Another embodiment of the invention is a method of delivering a transferable label to a target cell. A target cell comprising a protease having a proteolytic activity is contacted with a viral display package and a protease inhibitor. The viral display package comprises a transferable label, preferably an expressible polynucleotide, and a recombinant viral envelope protein. The recombinant viral envelope protein comprises in sequential order (I) a receptor-binding polypeptide which binds to an amphotropic receptor on the surface of the target cell, (ii) a protease cleavage site for the protease and (iii) a fusion-mediating polypeptide which binds to an ecotropic receptor on the surface of the target cell.

The receptor-binding polypeptide is preferably a receptor-binding domain of an amphotropic viral envelope protein (4070A). The fusion-mediating polypeptide is preferably a fusion-mediating domain of an ecotropic viral envelope protein, such as a Moloney murine leukemia virus envelope protein.

The target cell is a eukaryotic cell, preferably a mammalian cell, even more preferably a human cell. The target cell can be present in a mammalian or human body or can be in vitro.

In a preferred embodiment, the target cell expresses amphotropic virus receptors, but does not express ecotropic virus receptors, for example, an 'unmodified' human cell line. Cells such as lymphocytes and bone marrow cells are therefore useful according to the invention, provided they are transfected or subject to infection with a retrovirus, e.g., GALV.

Transfer of the transferable label from the viral display package to the target cell is dependent upon inhibition of the proteolytic activity of the protease produced by the target cell. A greater amount of transferable label is thereby delivered to the target cell in the presence of the protease inhibitor relative to the absence of the protease inhibitor. Alternatively, a plurality of target cells are contacted with a plurality of viral display packages and a protease inhibitor. In this case, the transferable label is delivered to a number of target cells, or to a greater number of target cells, in the presence of the protease inhibitor relative to the absence of the protease inhibitor.

Thus, the present invention provides an innovative approach to the identification of protease inhibitors, as well as the delivery of transferable labels to a target cell in the presence of a protease inhibitor.

DETAILED DESCRIPTION

Figures 1A, 1B:
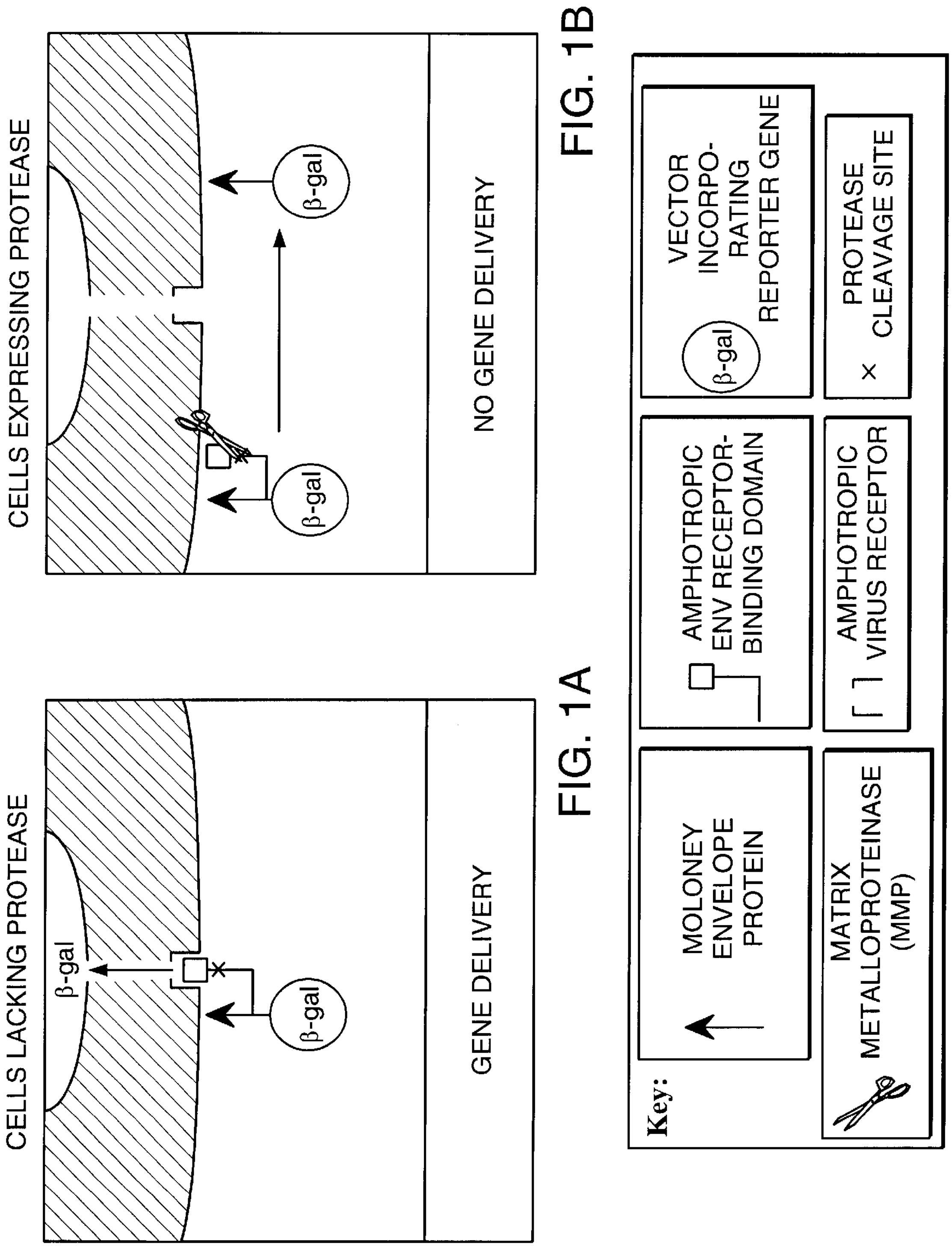
FIG. 1 is a schematic view of a method of inactivating viral display packages by protease activity. Chimaeric envelope proteins are generated by fusing the amphotropic Env receptor binding domain to the N-terminus of MoMLV Env, with a known protease cleavage site(x) situated between the two domains. Such 'AxMo' envelope proteins are incorporated into vectors containing the β-galacosidase reporter gene (β-gal). (a) These vectors can deliver β-gal reporter gene into cells via the interaction between the displayed amphotropic Env receptor binding domain and the amphotropic virus receptor. (b) If protease activity is present, the displayed domain is cleaved off and the vector is unable to deliver the reported gene.
Figures 2A, 2B:
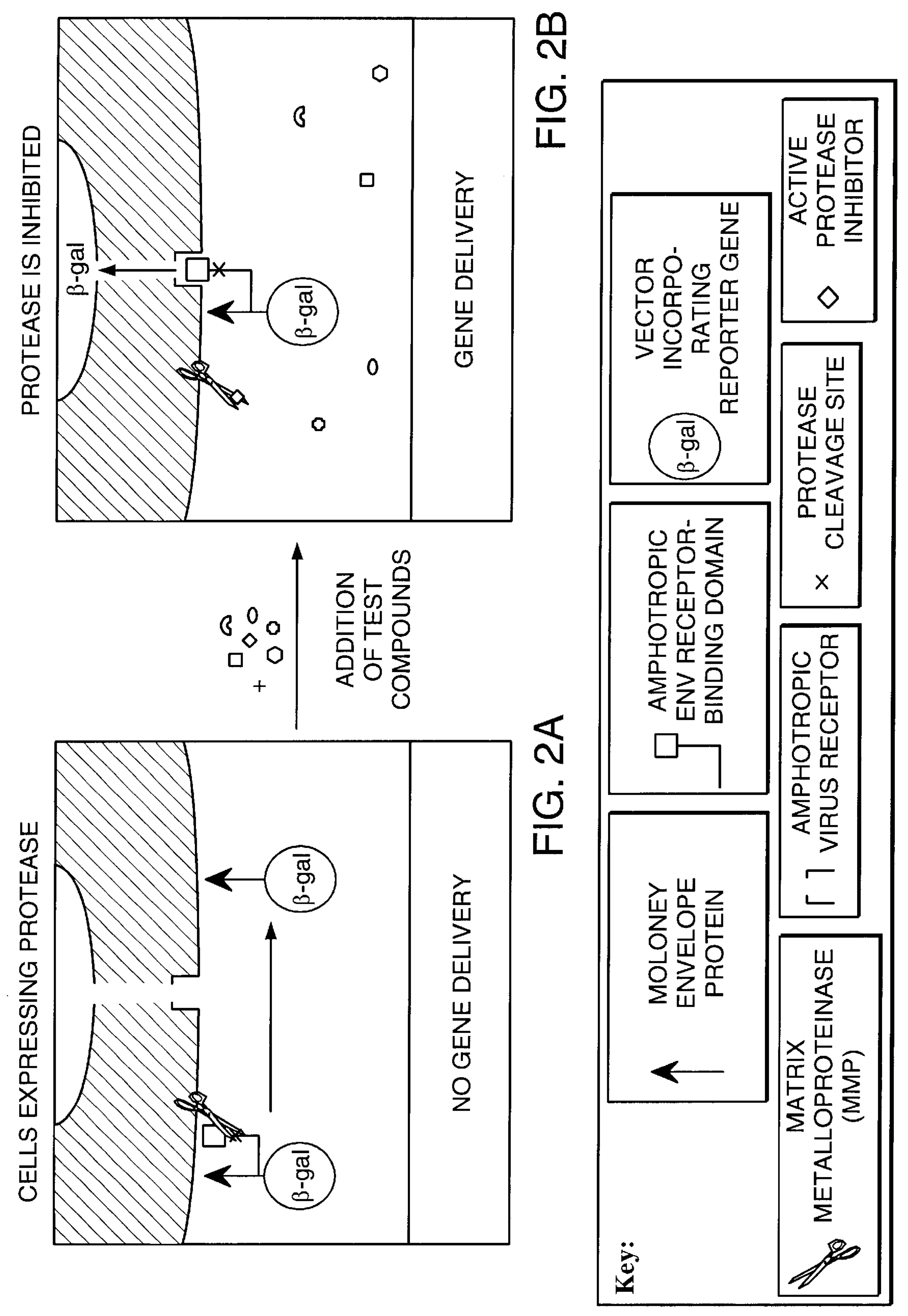
FIG. 2 is a schematic view of a screening assay for protease inhibitors. (a) AxMo vectors are unable to deliver the β-gal reporter gene into cells expressing protease 'X' and 4070A virus receptors. Protease 'x' cleaves the 4070A receptor-binding domain off the envelope protein leaving Moloney envelope (Mo), which is incapable of initiating infection in this context. (b) Upon addition of test compounds, those which are active protease inhibitors will prevent cleavage of AxMo envelope proteins, enabling β-gal gene transfer. Hence, protease inhibition is linked to reporter gene delivery.
Figure 3:
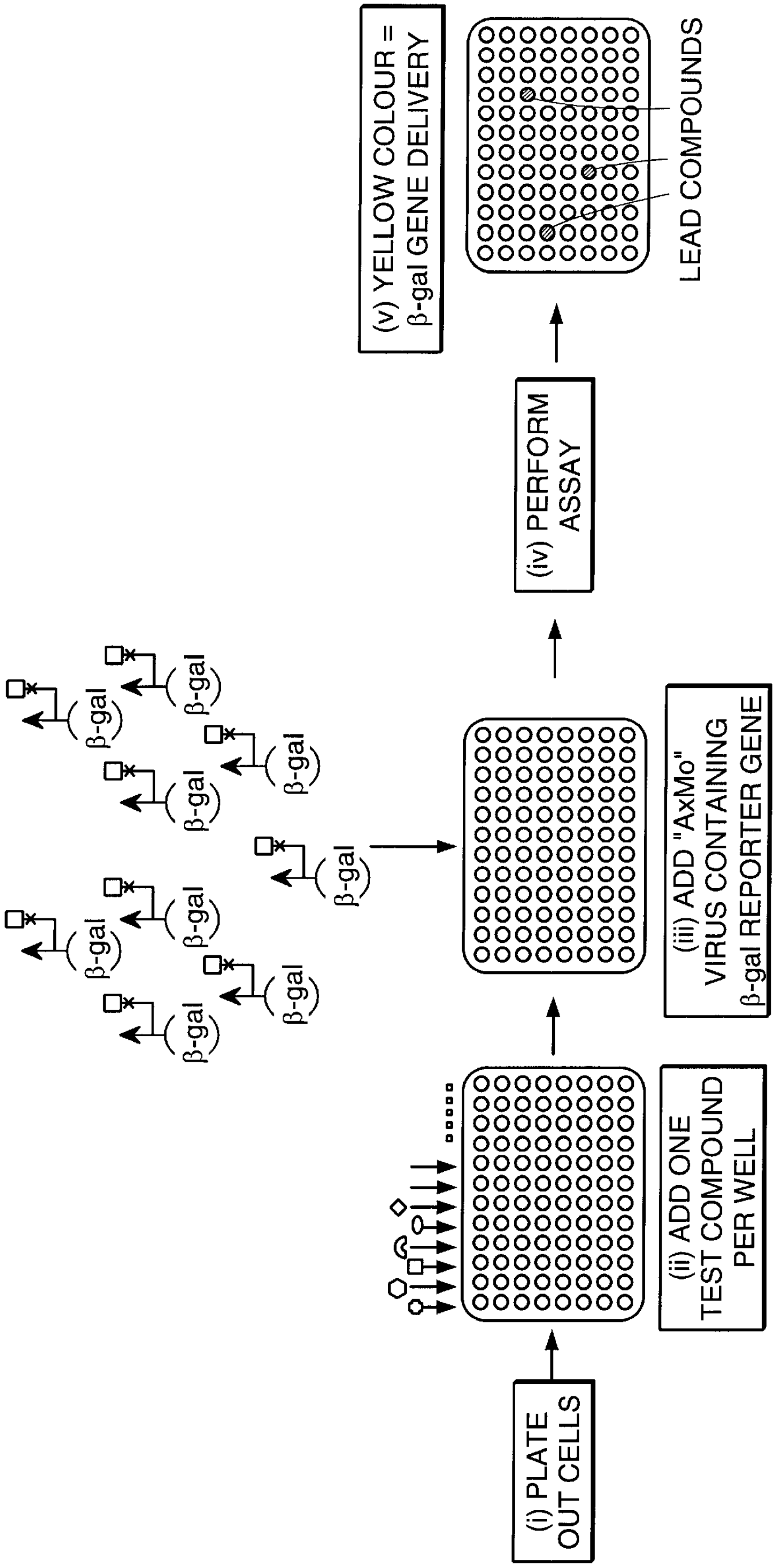
FIG. 3 is a schematic view of a high-throughput screening assay for protease inhibitors. The assay is performed as follows: i) Plate out cells which express 4070A virus receptors and the desired protease in 96-well plates, ii) Add compounds from a library, one compound per well, iii) Add 'AxMo' virus containing β-gal reporter gene, the vector is unable to deliver the reporter gene to cells expressing active protease, iv) Lyse cells and stain up with ONPG, (v) Read optical density in a spectrophotometer, relative to (no compound) controls. Increased OD at 405 nm correlates with increased reporter gene delivery and thus designates a compound with protease inhibitory activity.
Figure 4:
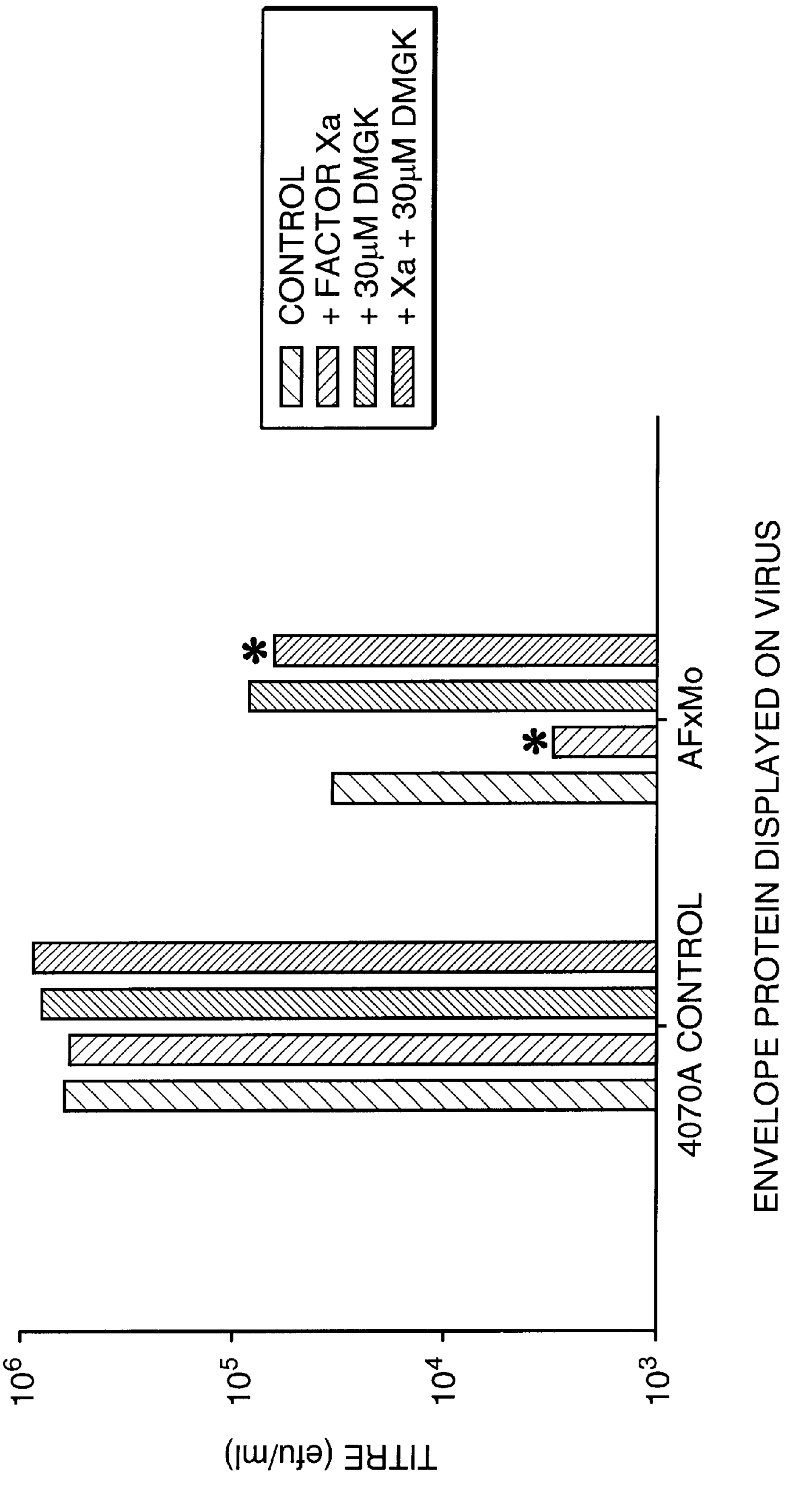
FIG. 4 is a graph demonstrating the results of a Factor Xa inhibitor assay in HT1080 Cells. The infectious titre of viruses bearing wild-type (4070A) and engineered (AXMO) envelope proteins on HT1080 cells was determined following treatment with or without Factor Xa protease and with or without DMGK (Xa inhibitor).
Figure 5:
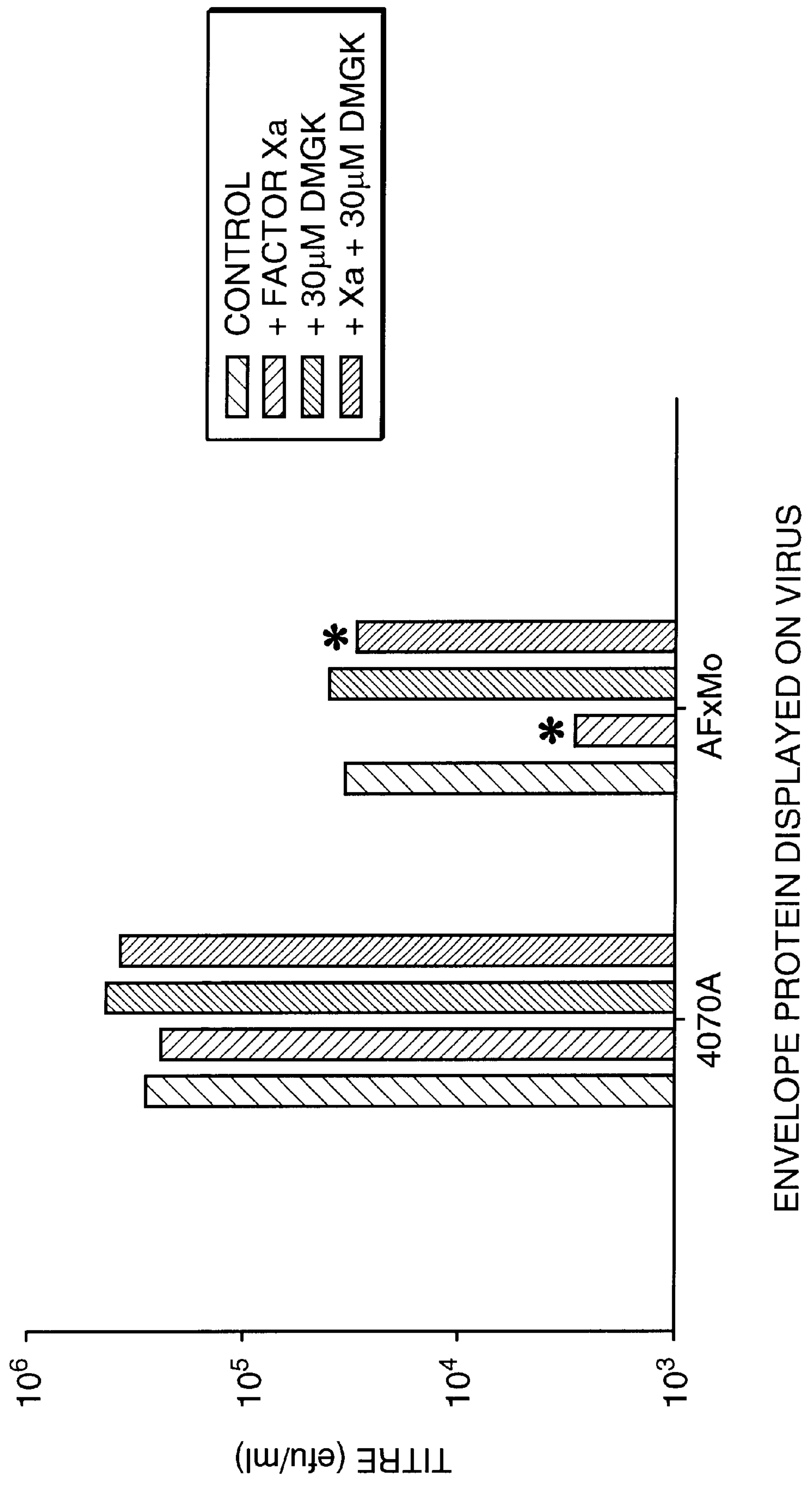
FIG. 5 is a graph demonstrating the results of a Factor Xa inhibitor assay in TE-671 Cells. The infectious titre of viruses bearing wild-type (4070A) and engineered (AXMO) envelope proteins on TE 671 cells was determined following treatment with or without Factor Xa protease and with or without DMGK (Xa inhibitor).
Figure 6:
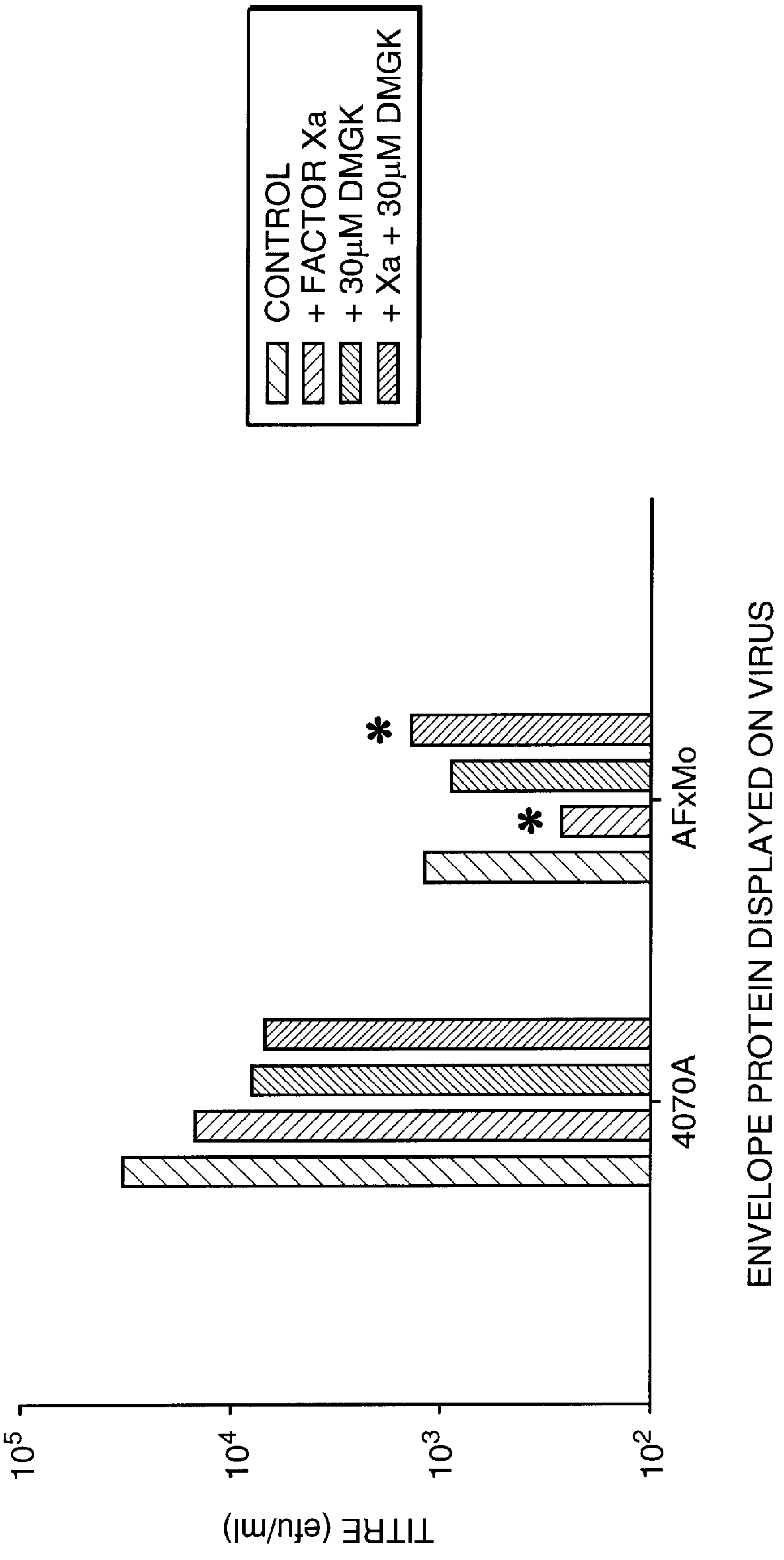
FIG. 6 is a graph demonstrating the results of a Factor Xa inhibitor assay in HT 1080 Recl clone 9 cells. The infectious titre of viruses bearing wild-type (4070A) envelope proteins on HT1080 Recl clone 9 cells was determined following treatment with or without Factor Xa protease and with or without DMGK (Xa inhibitor).
Figure 7:
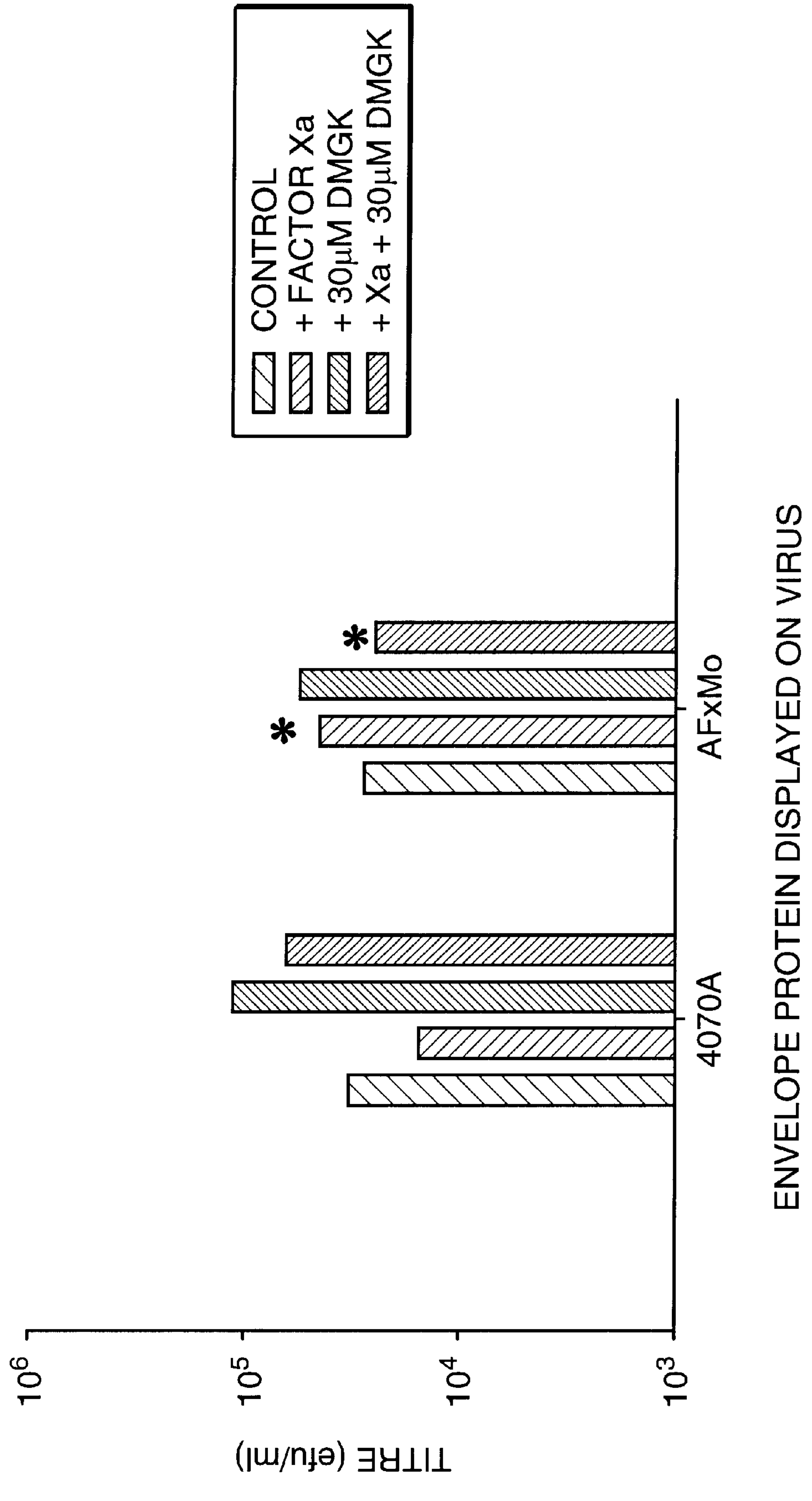
FIG. 7 is a graph demonstrating the results of a Factor Xa inhibitor assay in NIH 3T3 cells. The infectious titre of viruses bearing wild-type (4070A) and engineered (AXMo) envelope proteins on NIH 3T3 cells was determined following treatment with or without Factor Xa protease and with or without DMGK (Xa inhibitor).
Figure 8:
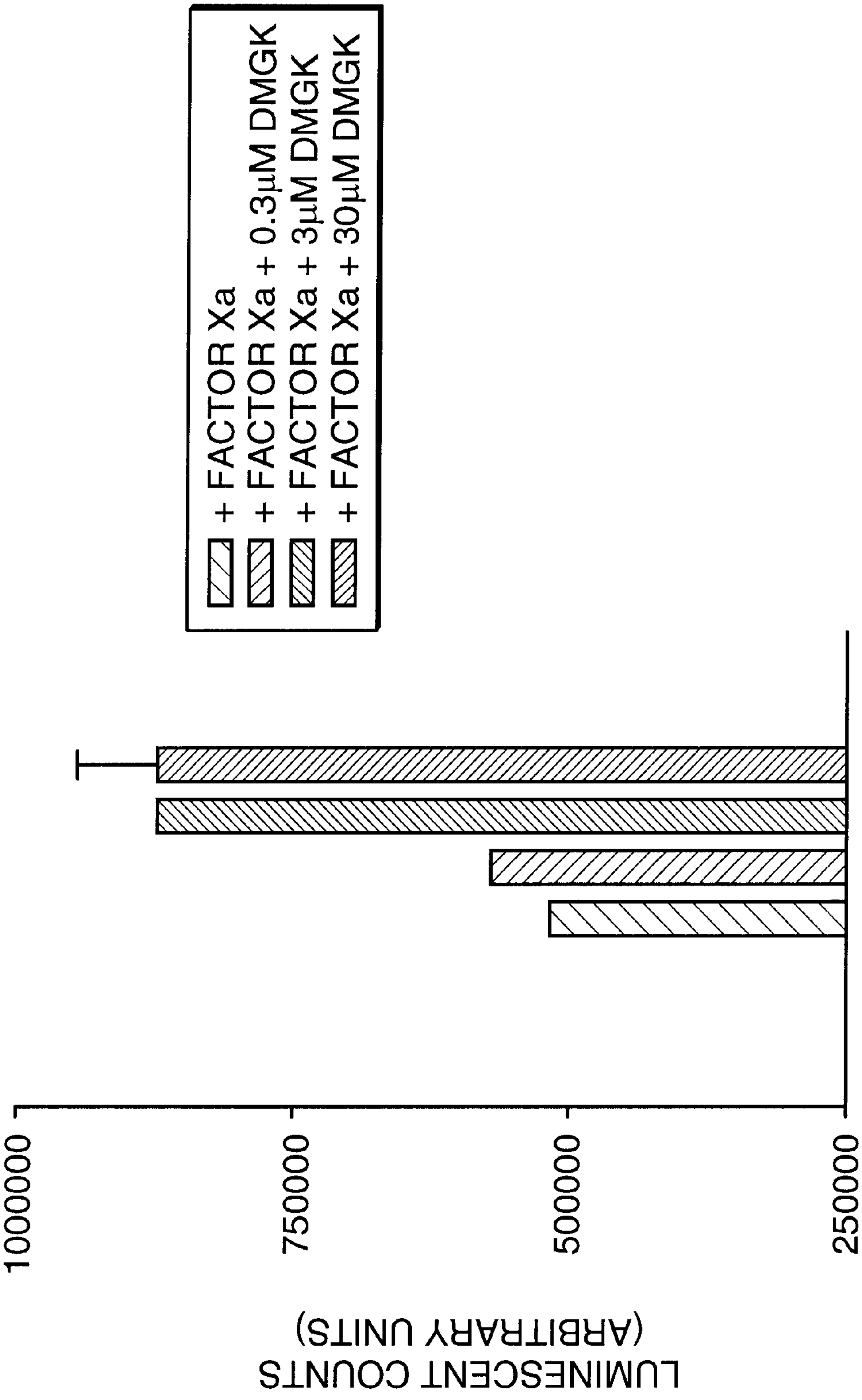
FIG. 8 is a graph demonstrating the effect of increasing concentrations of DMGK inhibitor on factor Xa cleavage of engineered (AXMo) envelope proteins in HT1080 cells. Quantitative luminescent readout showing the effect of increasing concentrations of DMGK inhibitor upon factor Xa cleavage of engineered (AXMo) envelope proteins.
Figure 9:
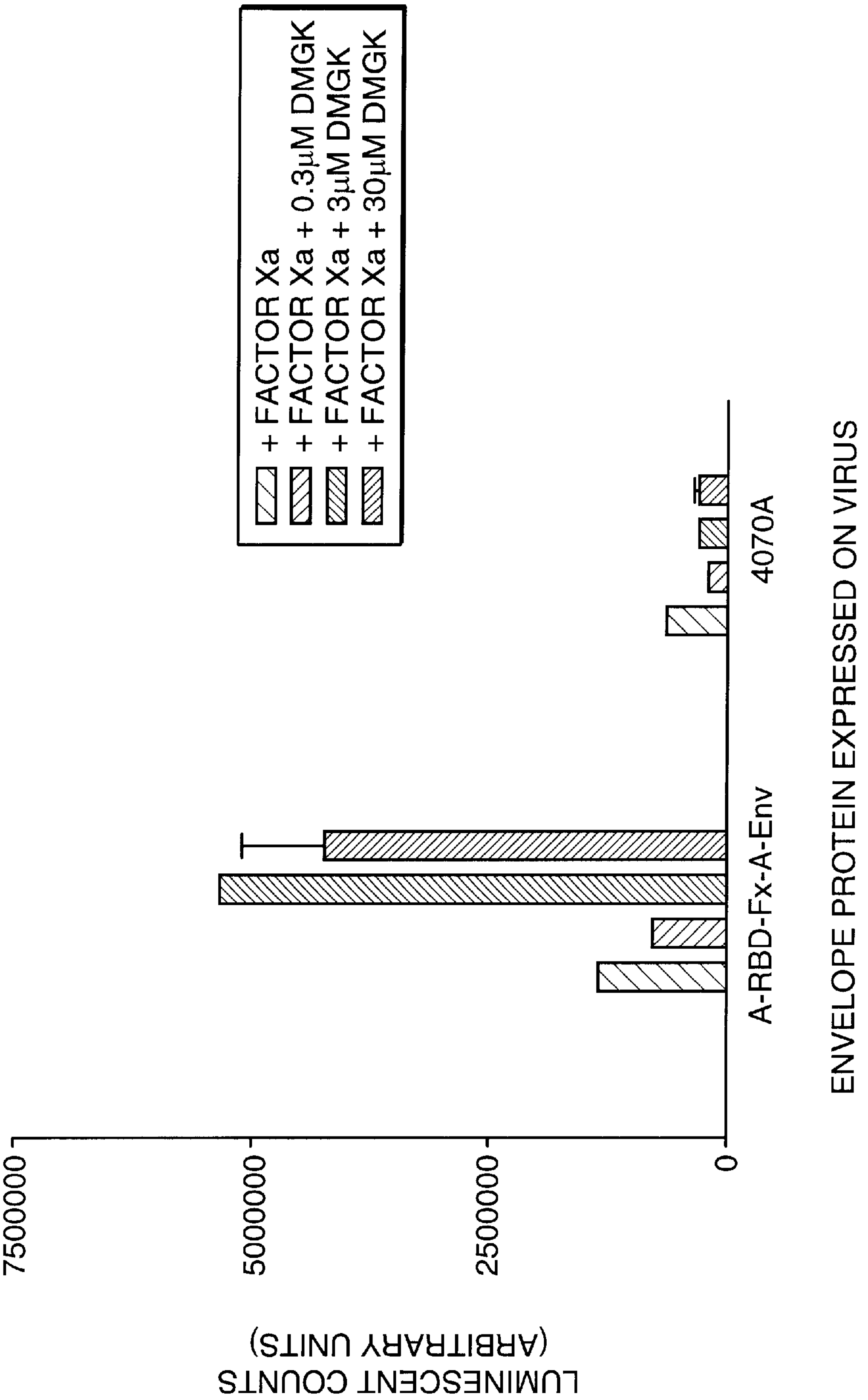
FIG. 9 is a graph demonstrating the effect of increasing concentrations of DMGK inhibitor on factor Xa cleavage of engineered (ARBDXA) and wild-type (4070A) envelope proteins in HT1080 cells, using an HTS format. Quantitative luminescent readout showing the effect of increasing concentrations of DMGK inhibitor upon factor Xa cleavage of engineered (ARBDXA) and wild-type (4070A) envelope proteins.
Figure 10:
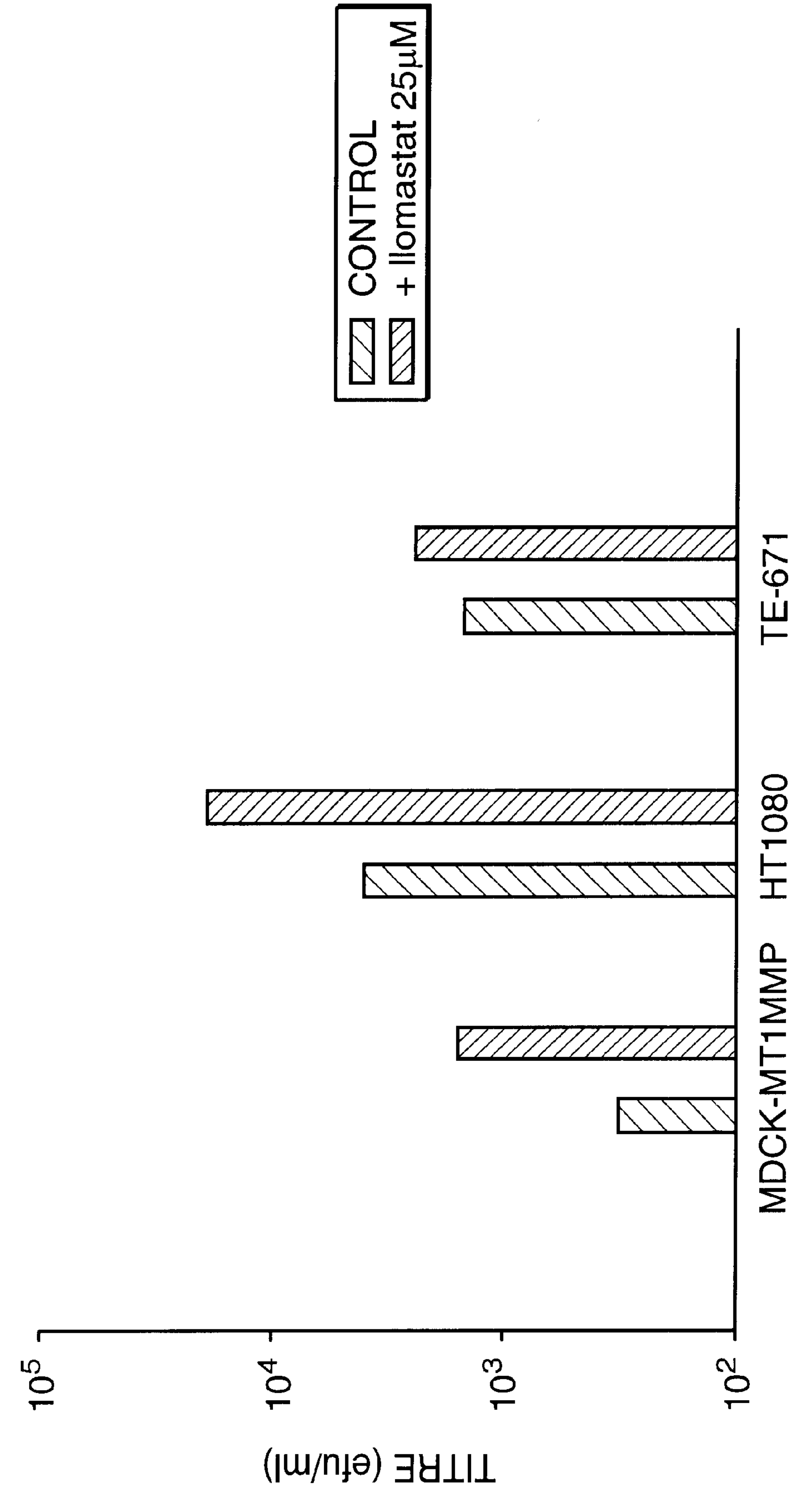
FIG. 10 is a graph demonstrating the effect of Ilomastat metalloproteinase inhibitor on the infectious titre of viruses expressing engineered (ARBDMMPA) envelope proteins in various cell lines. The infectious titre of viruses being engineered (ARBDMMPA) envelope proteins on 3 cell lines was determined following treatment with or without Ilomastat metalloproteinase inhibitor.
Figure 11:
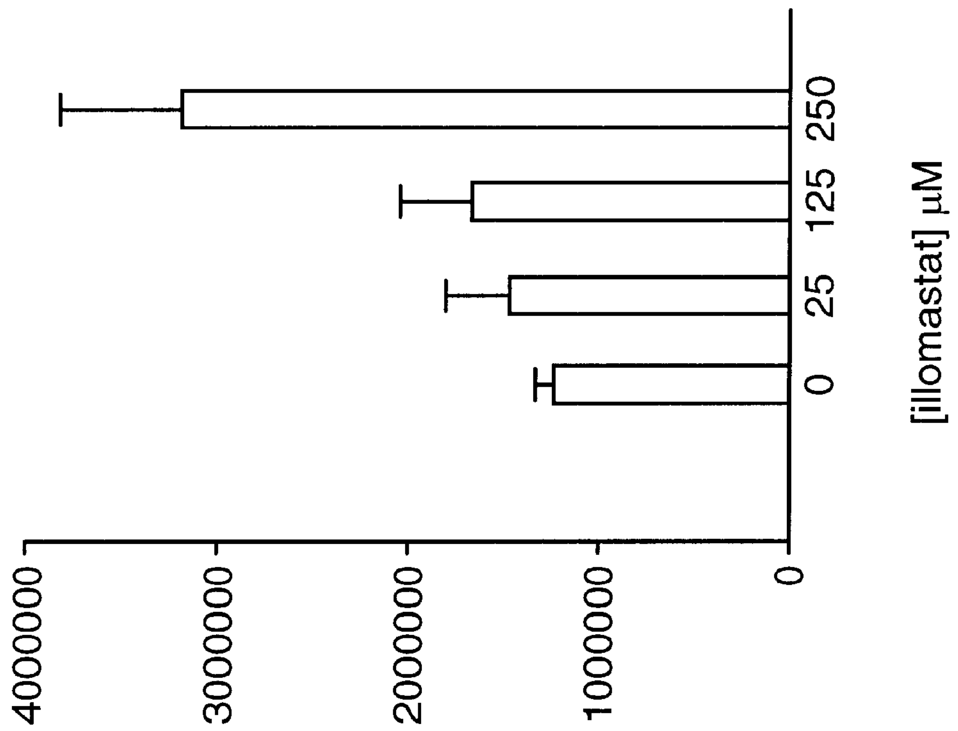
FIG. 11 is a graph demonstrating the effect of increasing concentrations of Ilomastat inhibitor on endogeous metalloproteinase cleavage of engineered (ARBDMMPA) envelope proteins in HT1080 cells, using an HTS format. Quantitative luminescent readout showing the effect of increasing concentrations of Ilomastat inhibitor upon endogenous metalloproteinase cleavage of engineered (ARBDMMPA) envelope proteins.

According to the invention, a target cell having proteolytic activity is contacted with a viral display package containing a transferable label in the presence of a test substance. The viral display package displays a recombinant viral envelope protein which comprises a receptor-binding polypeptide, a fusion-mediating polypeptide, and a protease cleavage site located between the receptor-binding polypeptide and the fusion-mediating polypeptides. Both of the receptor-binding and fusion-mediating polypeptides of the recombinant viral envelope protein are required for transfer of the transferable label to the target cell. A greater amount of transferable label in a target cell and/or a greater number of target cells which comprise the transferable label in the presence of the test substance relative to the absence of the test substance permits identification of test substances with protease inhibiting activity.

Without being bound to any one mechanism of action, it is believed that production of a protease by the target cell which can recognize the protease cleavage site in the recombinant viral envelope protein and hydrolyze a peptide bond within the site results in cleavage of the receptor-binding polypeptide from the recombinant viral envelope protein, and such cleavage prevents or substantially precludes transfer of the transferable label to the target cells. In the presence of a protease inhibitor, however, the receptor-binding polypeptide is not cleaved by a protease and transfer of the transferable label to the target cells occurs or occurs at an increased level. Thus, a test substance which causes an increased amount of the transferable label in a target cell or which increases the number of target cells comprising the transferable label is identified as an inhibitor of the protease produced by the target cell.

This discovery permits the identification of inhibitors of proteases for which a protease cleavage site has been identified, as well as inhibitors of proteases which may be unknown, i.e., a protease that has not yet been cloned, identified, characterized, and/or purified, or inhibitors of variant proteases (that may have been mutated at specific positions, or randomly mutated), which have a particular (different) substrate specificity.

One particular advantage of the present invention is that because eukaryotic cells are used as target cells in the screening assay, protease inhibitors are identified in a physiological environment (i.e., an environment in which target cells function in a way which is similar to the way the same target cells function in an intact animal) and can therefore be expected to be active in a physiological environment.

Another advantage is that the protease inhibitory activity of a test substance produces a positive read-out; that is, a positive result (identification of a protease inhibitor) is reflected by a positive signal (detection of the transferable label), thereby reducing the number of false positive results in a screening assay.

Another advantage is that it is not necessary to clone or purify the protease to be inhibited. Thus, the identified protease inhibitors can be used to inhibit protease activity even before the inhibited protease has been identified and cloned.

Protease inhibition is useful for a variety of purposes. For example, protease inhibitors can be used for the therapeutic treatment of conditions such as cancer, rheumatoid arthritis or other autoimmune diseases, inflammation, or infections such as AIDS, hepatitis, or herpes.

Methods of the invention can also be used to deliver a transferable label, such as an expressible polynucleotide, from a viral display package to a target cell via the interaction of the fusion-mediating polypeptide and its cognate receptor on the surface of the target cell. In this embodiment, the recombinant envelope protein displayed by the viral display package preferably comprises, from N- to C-terminus, an amphotropic receptor-binding polypeptide, a protease cleavage site for a protease produced by the target cell, an inhibitor of the protease and an ecotropic fusion-mediating polypeptide. The target cell expresses the cognate amphotropic receptors for the amphotropic receptor-binding polypeptide, and preferably does not express cognate receptors for the ecotropic polypeptide. Where the ecotropic receptor is absent on the target cell, it is believed that the recombinant envelope protein cannot initiate infection of the target cell after the amphotropic receptor binding domain has been removed by proteolytic cleavage. Hence, a protease inhibitor prevents cleavage of the receptor binding domain from the recombinant envelope protein, thereby permitting gene transfer.

If the protease is inhibited, the transferable label can be delivered to the target cell by fusion of the viral display package and target cell membranes. Thus, delivery of the transferable label to the target cell can be controlled by varying the level of protease inhibitor present in this system.

Proteases which can be Inhibited According to the Invention

A "protease" is an enzyme, also called an endoprotease, having a "proteolytic activity" which can be inhibited or substantially inhibited according to the invention. The proteolytic activity hydrolyzes a peptide bond between a pair of amino acids located in a polypeptide. Proteolytic activity of a protease is "substantially inhibited" if the ability of the protease to hydrolyze such peptide bonds is decreased by at least 10, 25, 50, 75, 85, 90, or 95% relative to the ability of the protease to hydrolyze such peptide bonds in the absence of a protease inhibitor.

Proteases are typically defined by reference to the nucleophile in the catalytic center of the enzyme. The most common nucleophiles arise from the side chains of serine, aspartic acid, and cysteine, resulting in families of proteases, such as serine proteases (Paetzel et al., *Trends Biochem. Sci.* 22, 28–31, 1997), aspartyl proteases (Spinelli et al., *Biochemie* 73, 1391–96, 1991), and cysteine proteases (Altschuh et al., *Prot. Eng.* 7, 769–75, 1994). Metalloproteases usually contain a zinc catalytic metal ion at the catalytic site (Klimpel et al., 1994, *Mol. Microbiol.*13, 1093–100). Examples of members of each of these protease families are provided in Table I.

TABLE I

Proteases and Protease Cleavage Sites (*indicates the peptide bond being hydrolyzed)

| Protease Family | Protease | Protease Cleavage Sites |
|---|---|---|
| serine | factor Xa | Ile-Glu-Gly-Arg* |
| serine | trypsin | Lys*, Arg* |
| serine | chymotrypsin | Tyr*, Phe*, Leu*, Ile*, Val*, Trp*, and His* at high pH |
| serine | thrombin | Arg* |
| serine and cysteine variants | peanut mottle potyvirus NIa protease | Glu-Xaa-Xaa-Tyr-Xaa-Gln* (Ser/Gly) |
| cysteine | papain | Arg*, Lys*, Phe*X |
| cysteine | bromelain | Lys*, Ala*, Tyr*, Gly* |
| cysteine | cathepsin B | Arg*Arg, Phe*Arg |
| cysteine | cathepsin L | Phe*Arg |
| aspartyl | HIV protease | Phe*Pro |
| aspartyl | *S. cerevisiae* yapsin 2 | Lys*, Arg* |
| aspartyl | cathepsin D | Phe*Phe, Phe*Lys, Leu*Phe, Leu*Tyr |
| metallo- | thermolysin | *Tyr, *Phe, *Leu, *Ile, *Val, *Trp, and *His |
| metallo- | peptidyl-Lys metalloendopeptidase | Xaa*Lys |
| metallo- | peptidyl-Asp metalloendopeptidase | Xaa*Asp, Xaa*Glu, Xaa*Cys |
| metallo- | coccolysin | *Leu, *Phe, *Tyr, *Ala |
| metallo- | autolysin | Leu-Trp-Met*Arg-Phe-Ala |
| metallo- | human neutrophil collagenase (MMP-8) | Gly-Leu-Ser-Ser-Asn-Pro*-Ile-Gln-Pro |
| metallo- | gelatinase A (MMP-2) | Pro-Gln-Gly*Ile-Ala-Gly-Gln |

Proteases of particular interest include those involved in infectious diseases, such as HIV and hepatitis C, and in malignant tumors. For example, test substances which could decrease or eliminate the activity of the hepatitis C virus (HCV) protease NS3 can be tested by employing as the protease cleavage site in a recombinant viral envelope protein the preferred substrates for the NS3 protease-NS4A cofactor complex which occur in the HCV polyprotein (see Zhang et al., *J. Virol.* 71, 6208–13; Leinbach et al., *Virology* 204, 163–69; Urbani et al., *J. Biol. Chem.* 272, 9204–09).

Similarly, test substances can be screened for the ability to inhibit one or more metalloproteases which are present in malignant tumors. For example, specific cleavage at residue 587 of the 2 subunit of laminin-5 by matrix metalloprotease-2 induces migration of breast epithelial cells in breast tumors (Gianelli et al., *Science* 277, 225–28). HL-60 leukemia cells secrete MMP-9 as well as a 45 kd matrix metalloprotease; the 45 kd metalloproteinase cleaves the peptide bond between Ala and Gly in the synthetic substrate Pro-Gln-Gly-Ile-Ala*Gly-Gln-Arg (Dittmann et al., *Exp. Hematol.* 23, 155–60). Recombinant viral envelope proteins comprising such protease cleavage sites can be used to screen for test substances which inhibit the metalloproteases expressed in these tumors.

Protease Inhibitors Identifiable according to the Invention

A "protease inhibitor" which can be identified according to the methods disclosed herein is a molecule which decreases the proteolytic activity of a protease and thereby permits substantial transfer of a transferable label from a viral display package to a target cell. "Substantial transfer" is any amount of transfer of the transferable label from the viral display package to the target cell which permits detection of the transferable label in the target cell or detection of a greater number of target cells comprising the transferable label.

A "greater number" of target cells which comprise the transferable label is any number of target cells which is at least 1, 2, 5, 10, 20, 50, or 100 more than the number of target cells which comprise the transferable label in the absence of a protease inhibitor. The "amount" of label transferred in the presence of an inhibitor is considered a "greater amount" if it is at least 10, 20, 25, 50, 75, 85, 90, 95, 98, 99, or 100%, or at least 3-, 4-, 5-, 6-, 7-, 8-, 9-, or 10-fold greater than the amount of transferable label that is transferred from a viral display package to a target cell in the absence of the protease inhibitor. If no amount of label is transferred in the absence of the protease inhibitor, then any detectable label in the presence of the inhibitor is indicative of inhibition and is a "greater amount."

Competitive, uncompetitive, and noncompetitive inhibitors, as well as inhibitors which bind irreversibly to the protease, are included within the definition of protease inhibitors (see Lehninger, Biochemistry, 2d ed., 1975, at pages 197–201). Preferably, a protease inhibitor is specific for a particular protease, but molecules which decrease proteolytic activity of more than one protease, such as two or more members of a family of proteases, are also protease inhibitors.

Test Substances

"Test substances" which can be screened for protease inhibiting activity can be pharmacologic agents already known in the art or can be compounds previously unknown to have any pharmacological activity. Test substances can be naturally occurring or designed in the laboratory. They can be isolated from microorganisms, animals, or plants, or can be produced recombinantly or synthesized by chemical methods known in the art. Preferably, test substances are small molecules from compound libraries.

Protease Cleavage Sites

A "protease cleavage site" according to the invention is a contiguous sequence of amino acids connected by peptide bonds which contains (I) a pair of amino acids which is connected by a peptide bond that is hydrolyzed by a particular protease. Optionally, a protease cleavage site according to the invention may include one or more amino acids on either side of the peptide bond to be hydrolyzed, to which the catalytic site of the protease also binds (Schecter and Berger, *Biochem. Biophys. Res. Commun.* 27, 157–62, 1967), or the cleavage site and recognition site on the protease substrate may be two different sites that are separated by one or more (e.g., two to four) amino acids. If the protease recognition and cleavage sites are distinct sites on the protease substrate, then the recognition site is positioned between the receptor-binding polypeptide and the fusion-mediating polypeptide, and the cleavage site is present on one or the other side of the recognition site.

The specific sequence of amino acids in the protease cleavage site depends on the catalytic mechanism of the protease, which is defined by the nature of the functional group at the protease's active site, as discussed above. For example, trypsin hydrolyzes peptide bonds whose carbonyl function is donated by either a lysine or an arginine residue, regardless of the length or amino acid sequence of the polypeptide chain. Factor Xa, however, recognizes the specific sequence Ile-Glu-Gly-Arg and hydrolyzes peptide bonds on the C-terminal side of the Arg.

Thus, a protease cleavage site comprises at least 2, 3, 4, 5, 6, 7, 8, 9, or 10 or more amino acids. Optionally, additional amino acids (such as amino acid linker sequences) can be present at the N-terminus and/or C-terminus of the cleavage site. a protease cleavage site according to the invention also can be a variant of a cleavage site of a known protease, such as the cleavage sites shown in Table I, above.

Optionally, a protease cleavage site can be selected using a method such as that taught in U.S. Pat. No. 5,780,279. This method involves producing a fusion gene encoding a polypeptide, a substrate peptide, and at least a portion of a phage coat protein. The DNA encoding the substrate peptide is mutated at one or more codons to generate a family of mutants. The mutant fusion proteins are expressed on the surface of a phagemid particle and then exposed to a protease which may or may not recognize and cleave the mutant substrate peptide. If cleavage does occur, the polypeptide will become dissociated from the phagemid particle, and when the phagemid particle is contacted with an affinity molecule specific for the polypeptide, it will not bind. Thus, phagemid particles which express mutant fusion proteins comprising a substrate peptide which can be cleaved by a protease can be separated from those which do not express such fusion proteins. The substrate peptide so identified can be used to provide a protease cleavage site for use in methods of the invention.

Viral Display Packages

"Viral display packages" are well known in the art (see, e.g., U.S. Pat. No. 5,723,287). Viral display packages of the invention display recombinant viral envelope proteins on their surface. Production of such viral display packages is taught, for example, in U.S. Pat. No. 5,723,287 and in Chadwick et al. (*J. Mol. Biol.* 285, 485–94, 1999). Briefly, viral packaging cells, such as Psi 2, TELCeB.6, and PA317, are conveniently used to produce viral display packages. The packaging cells comprise a transferable label, which is packaged into viral display packages, and a polynucleotide having a coding sequence for a recombinant viral envelope protein. "Members" of a plurality of viral display packages refers to either a portion of the plurality, e.g., 10, 20, 30 40, 50, 60, 70, 80, or 90%, or to the entire plurality.

Recombinant Viral Envelope Proteins

A "recombinant viral envelope protein" comprises the following three components from N- to C-terminus: (1) a receptor-binding polypeptide, (2) a protease cleavage site, and (3) a fusion-mediating polypeptide. Typically, the receptor-binding and fusion-mediating polypeptides are derived from viral envelope proteins. The receptor-binding and fusion-mediating polypeptides can be derived from the same or from different viral envelope proteins. The fusion-mediating polypeptide can be an intact envelope protein.

Receptor-Binding Polypeptides

The receptor-binding polypeptide initiates delivery of the transferable label from a viral display package to a target cell (Cosset et al., 1995, *J. Virol.* 69, 6314–22). The fusion-mediating polypeptide mediates fusion between the viral display package and the outer membrane of the target cell (Cosset et al., 1995). The "receptor-binding polypeptide" refers to a polypeptide which is capable of binding to a cognate viral envelope receptor on the surface of the target cell.

The receptor-binding polypeptide may be a protein that is intact for the full length in which it is produced in nature, or it may be a domain of a full-length protein that retains the ability to bind to the cognate cell surface receptor. Such portions are also receptor-binding polypeptides.

It is important that the receptor-binding polypeptide retains the ability to conserve post-translational processing and receptor-binding activities. However, certain alterations, such as mutations, deletions, or additions, can be made to the receptor-binding polypeptide which do not significantly affect these functions, and receptor-binding polypeptides with such modifications are considered "substantially intact".

In one embodiment the receptor-binding polypeptide is a receptor-binding domain of a viral envelope protein, such as an amphotropic (4070A) envelope protein, or a domain or polypeptide capable of binding to a cell surface receptor and thereby initiating delivery of a gene to the target cell bearing the surface receptor.

An "amphotropic envelope protein" refers to any domain or polypeptide capable of binding to a cell-surface receptor (one example being 4070A env, which binds to Ram-1/Pit-2/Glvr-2) and initiating gene delivery thereby.

Other receptor-binding polypeptides useful in the invention include receptor binding domains of envelope proteins from viruses such as Moloney murine leukemia virus, 4070A, and gibbon ape leukemia virus (Cosset et al., 1995). Binding of a receptor-binding polypeptide to a receptor (e.g., MMLV env binding to the ecotropic CAT-1 receptor) can be detected using binding assays familiar to those in the art. For example, a candidate receptor-binding polypeptide can be conjugated to a detectable label, such as a fluorescent, chemiluminescent, or radioactive label; the labeled polypeptide can then be detected on the target cell surface. A displacement assay can also be used, in which the ability of a candidate receptor-binding polypeptide to displace a receptor-binding polypeptide is assessed. The minimum level of binding or displacement useful according to the invention would be on the order of 10% or more, 20% or more, 50% or more, and even up to 100%.

Fusion-mediating Polypeptides

A "fusion-mediating polypeptide" mediates fusion between the membrane of a viral display package and a target cell membrane, i.e., is capable of permitting transfer of a transferable label from a viral display package to a target cell. Fusion-mediating polypeptides which increase the amount of transferable label detectable in target cell at least 10%, 25%, 50%, 75%, or 100% or more, e.g., 2-fold, 5-, 10-, 20-, 50-, 100- or 1000-fold or more, relative to the amount of transferable label detectable in the target cell in the absence of the polypeptide are fusion-mediating polypeptides. Fusion-mediating polypeptides suitable for use in a recombinant viral envelope protein include substantially intact viral envelope proteins of any retrovirus, viruses such as Moloney murine leukemia virus, 4070A, and gibbon ape leukemia virus, as well as the fusion-mediating (transmembrane) subunits of these envelope proteins (Cosset et al., 1995).

Viral Envelope Proteins Comprising Protease Cleavage Sites

In one embodiment, the recombinant viral envelope protein is a "substantially intact" viral envelope protein in which a protease cleavage site has been inserted between the receptor-binding polypeptide (a sub-domain of SU) and the "proline-rich" domains of Ampho SU. The receptor binding domain of SU and proline-rich domains of Ampho SU are described in Battini et al., 1995, J. Virol. 69: 713–719; Battini et al., 1996, J. Virol. 70: 4387–4393; and Lavillette et al., 1998, J. Virol. 72: 9955–65, the contents of which are hereby incorporated by reference.

In addition, or alternatively, a protease cleavage site may be inserted between the proline-rich domain and the C-terminal domains of SU. It is important that the viral envelope protein is substantially intact, i.e. retains all its domains, to conserve post-translational processing, oligomerization, viral incorporation, and fusogenic activities. However, certain alterations, such as mutations, deletions, or additions, can be made to the viral envelope protein which do not significantly affect these functions, and viral envelope proteins with such modifications are considered substantially intact.

A retroviral envelope protein, such as an envelope protein of a murine leukemia virus, e.g., Moloney murine leukemia virus or 4070A, may be used. The inserted protease cleavage site can be located at any position in the extracellular portion of the substantially intact envelope protein (SU and part of TM) that does not impair the function of the envelope protein and causes the envelope protein to become non-functional upon cleavage.

Recombinant Viral Envelope Proteins with Amphotropic and Ecotropic Domains

In another embodiment, a recombinant viral envelope protein comprises, from N- to C-terminus, (1) a receptor-binding polypeptide of an amphotropic virus envelope protein, (2) a protease cleavage site, and (3) a fusion-mediating polypeptide of an ecotropic virus envelope protein. According to the invention a virus receptor binding domain may be fused with, or displayed on a substantially "intact" viral envelope protein (as described above) with a protease cleavage site between the receptor and envelope protein domains. For example, a Moloney leukemia virus receptor binding domain may be fused to a 4070A envelope protein with a protease cleavage site in between.

The invention also encompasses a recombinant viral envelope protein in which the receptor-binding polypeptide is fused to the fusion-mediating polypeptide via an adapter polypeptide which permits modulation of the level of gene delivery via the receptor-binding domain interaction with its cognate receptor, and/or via interaction of the fusion-mediating polypeptide with its cognate receptor, if the latter receptor is present on the cell. (See Valsesia-Wittmann et al., 1997, "Receptor cooperation in retrovirus entry: recruitment of an auxiliary entry mechanism after retargeted binding", EMBO J. 16(6);1214–23, hereby incorporated by reference.) Thus, as disclosed in Valsesia-Wittmann et al., the adapter may be a proline-rich domain from an MLV envelope protein.

Production of Recombinant Viral Envelope Proteins

Polynucleotides encoding recombinant viral envelope proteins can be produced using recombinant DNA technology or can be synthesized using standard nucleic acid synthesis techniques and expressed in a cell-free or cell-based expression system, as is known in the art. Alternatively, the proteins themselves can be synthesized, for example, by solid-phase protein synthesis.

Transferable Labels

A "transferable label" can be any label whose presence can be detected in the target cell upon fusion of the viral display package and the target cell membrane, such as a fluorescent, radioactive, or chemiluminescent tag. If desired, the transferable label may be a gene encoding a selectable marker or a reporter gene encoding a detectable product.

Genes encoding selectable markers are preferably antibiotic-resistance genes, such as a neomycin, puromycin, or phleomycin resistance gene. Reporter genes encode a detectable product, such as β-galactosidase, luciferase, β-glucuronidase, green fluorescent protein (GFP), autofluorescent proteins, including blue fluorescent protein (BFP), glutathione-S-transferase (GST), luciferase, horseradish peroxidase (HRP), or chloramphenicol acetyltransferase (CAT). Many such genes are known in the art. Transferable labels also include proteins which can be detected using immunochemical techniques employing antibodies which specifically bind to the protein product.

Target cells comprising transferable labels are detected by a method appropriate to the particular label used. For example, target cells comprising a selectable marker, such as an antibiotic resistance gene, are detected by culturing the cells in a medium containing the appropriate antibiotic, such that only cells to which the antibiotic resistance gene has been transferred will survive. Assays, such as immunological or colorimetric assays, are available and well-known in the art for detecting target cells comprising detectable labels such as those listed above. Such detection methods can be either qualitative or quantitative.

Target Cells

Target cells preferably express a protease having a proteolytic activity to be inhibited. The protease can be a known protease or can be a protease which has not yet been identified, for which a cleavage site is known. Cells which express proteases can be obtained, for example, from a tumor, a tissue which is inflamed, a tissue which is undergoing remodeling, such as a developing limb bud, or a tissue which is involved in wound healing. Cells comprising pathogens, such as HIV, rhinoviruses, hepatitis viruses, herpes viruses, or other infectious agents which express proteases, can also be used as target cells. Cells which express proteases can be identified, for example, using protease assays employing substrates which produce a detectable product, such as a chromogenic or fluorescent substrate. Substrates and protease assay kits are commercially available from companies such as Molecular Probes, Inc., Promega, and CLONTECH.

Alternatively, a polynucleotide encoding a particular protease or a modification of a particular protease can be introduced into a target cell using well-known methods, such as DEAE- and calcium phosphate-mediated transfection and electroporation. Polynucleotides encoding proteases can be obtained, for example, from cells such as those mentioned above, or can be produced recombinantly or synthetically. The polynucleotides can then be mutated, either randomly or at specific sites, to produce polynucleotides encoding variations of known protease sequences which have altered substrate specificity. Site-specific mutagenesis is taught, for example, in Watkins et al., *Biotechniques* 15,700–704 (1993), Weiner et al., *Gene* 126, 35–41 (1993), and Weiner et al., *Gene* 151,1/9–123 (1994). Optionally, polynucleotides encoding particular protease variations can be synthesized directly.

Cells which can be transfected with a polynucleotide encoding a protease and used as target cells include, but are not limited to, members of established cell lines such as NIH 3T3 cells (ECACC no. 85111801), Colo 205 cells (ECACC no. 87061208), Jurkat E6.1 cells (ECACC no. 88042803), A431 cells (ATCC CRL1555), TE 671 cells (ATCC CRL8805), or HT 1080 (ATCC CCL121).

Target cells also preferably express on their surface a receptor for the receptor-binding polypeptide present in the recombinant viral envelope protein. For example, if a Moloney murine leukemia virus receptor-binding polypeptide is used in a recombinant viral envelope protein, target cells preferably express the ecotropic CAT-1 receptor (Albritton et al., 1989, *Cell* 57, 569–76). Alternatively, if a 4070A murine leukemia virus receptor-binding polypeptide is used, target cells preferably express the amphotropic Pit-2/Ram-1 receptor (Vile and Russell, 1995, *Brit. Med. Bull.* 51, 12–30). The receptor can be naturally present on the target cell or a polynucleotide encoding the receptor can be introduced into the target cell, as described above. In one embodiment, target cells express on their surface an amphotropic receptor only.

"Members" of a plurality of target cells refers to either a proportion of the plurality, e.g., 10, 20, 30, 40, 50, 60, 70, 80, or 90%, or to the entire plurality.

Expressible Polynucleotides

An "expressible polynucleotide" according to the invention comprises a coding sequence for a protein and is capable of being expressed in a target cell of the invention. Expressible polynucleotides contain less than a whole chromosome and can be RNA or single- or double-stranded genomic or cDNA. Preferably the polynucleotides are isolated free of other cellular components, such as membrane components, proteins, and lipids. They can be made by a cell and isolated, or synthesized in the laboratory using an amplification method such as PCR or using an automatic synthesizer. Methods for purifying and isolating DNA are routine and are known in the art (for example, see Sambrook et al., Molecular Cloning, 2d ed., 1989; Perbal, A Practical Guide to Molecular Cloning, 2d ed., 1988). Optionally, an expressible polynucleotide comprises a promoter which is operatively associated with the coding sequence. A variety of effective promoters, such as the CMV and β-actin promoters, are known in the art and can be operatively linked to expressible polynucleotide molecules. Of course, the promoter must be selected to be operative in the particular target cell which is used in the method. The selection of appropriate promoters is well within the skill in the art.

Delivery of transferable labels to target cells

Transferable labels, particularly expressible polynucleotides, can be delivered to target cells according to the invention, for example, for therapeutic purposes or for use as a model system for optimizing delivery of transferable labels. In this embodiment, target cells express on their surface both an amphotropic receptor, such as a Pit-2/Ram-1 4070A receptor (Miller et al., 1994, *Proc. Natl. Acad. Sci. U.S.A.* 91(1), 78–82), and an ecotropic receptor, such as a CAT-1 receptor (Kavanaugh et al., 1991, *Nature* 352 (6337), 729–31). Pit-2 receptors are expressed by a wide variety of human tissues.

Expressible polynucleotides encoding a CAT-1 receptor, for example, can be introduced into a target cell to provide appropriate expression of the desired receptor(s). If necessary for the particular target cell type selected, expressible polynucleotides encoding an amphotropic receptor can also be introduced into human cells. Any appropriate method can be used to introduce expressible polynucleotides into target cells. Methods of introducing polynucleotides into cells are well known and include, but are not limited to, DEAE-and calcium phosphate-mediated transfection, electroporation, and use of lipid compositions, such as Superfect by QIAGEN. The number of amphotropic receptors expressed by the target cells is preferably higher by at least 25, 50, 75, or 100% or more than the number of ecotropic receptors expressed.

One or more target cells are contacted with a protease inhibitor and one or more viral display packages comprising a transferable label. The target cells preferably express high levels of an amphotropic receptor. In this embodiment, viral display packages comprise a recombinant viral envelope protein which comprises, from N- to C-terminus, (i) an amphotropic receptor-binding polypeptide which binds to the amphotropic receptor on the surface of the target cell, (ii) a protease cleavage site for a protease produced by the target cell, and (iii) an ecotropic fusion-mediating polypeptide which is capable of mediating fusion of the viral display package membrane with the target cell membrane via interaction with the ecotropic receptor on the target cell surface.

Little or no transfer of the transferable label can occur in the presence of the protease produced by the target cell, because the protease will cleave the receptor-binding polypeptide from the fusion-mediating polypeptide, thereby impairing delivery of the transferable label via interaction with the amphotropic receptor, allowing only limited interaction between the remaining ecotropic envelope protein and the small number of ecotropic receptors present on the target cells. If desired, the linker region between the displayed amphotropic RBD and the underlying ecotropic Env can be modified (e.g. to comprise a PRO-rich hinge (q.v.)), such that cleavage by a protease leaves the remaining ecotropic envelope protein still substantially impaired for gene delivery (displaying PRO-rich region). In other words, a construct of the type:

Ampho RBD-cleavage site-PROrich-Eco Env might be made. Upon cleavage this leaves:

PROrich-Eco Env

This 'construct' is substantially impaired for gene delivery since the PROrich domain acts as a 'blocking domain'. Essentially, this is another potential mechanism for 'setting' the level of gene delivery pre- and post-cleavage.

In the presence of a protease inhibitor, however, the receptor-binding polypeptide is not cleaved from the fusion-mediating polypeptide, and fusion between the viral display package and the target cell membranes can occur via interaction with the amphotropic receptor, thereby permitting delivery of the transferable label.

The level, rate, and/or timing of delivery of the transferable label to the target cell can be modulated by including varying amounts of the protease inhibitor, e.g., 1 nM to 1 mM, together with the viral display packages, as described below. Moreover, a whole range of proteins, peptides, antisense RNA transcripts and ribozyme sequences can be encoded within an expressible polynucleotide and delivered to a target cell for a therapeutic effect.

Target Cells to which Transferable Labels can be Delivered

The target cell produces a protease and is typically a mammalian cell, preferably a human cell, and can be either in situ, in a mammalian or human body, or in vitro, i.e. in a primary cell culture or in a continuous cell line. Target cells suitable for use in this embodiment of the invention include, but are not limited to, cells of a tumor, a tissue which is inflamed, a tissue which is undergoing remodeling, such as a developing limb bud, or a tissue which is involved in wound healing, protease negative cells into which the DNA coding for a protease has been introduced (thus making it protease positive), and/or protease negative cells to which the protease itself is added (as purified protein or in a mixture), preferably at a defined concentration. Cells comprising a pathogen, such as an HIV virus, a rhinovirus, a herpes viruses, a hepatitis virus, or other infectious agent which express proteases, also are suitable target cells. Cell lines which can provide target cells include NIH 3T3 cells (ECACC no. 85111801), Colo 205 cells (ECACC no. 87061208), Jurkat E6.1 cells (ECACC no. 88042803), A431 cells (ATCC CRL1555), SW480 cells (ATCC CCL228), and HL-60 (ATCC CCL-240). Cells which express a protease can be identified, for example, using protease assays employing substrates which produce a detectable product, such as a chromogenic or fluorescent substrate. Substrates and protease assay kits are commercially available from companies such as Molecular Probes, Inc., Promega, and CLONTECH.

Compositions Comprising Viral Display Packages and Protease Inhibitors

Viral display packages and protease inhibitors can be present together in a composition which typically comprises a physiological carrier suitable for administration to mammals, particularly to humans. Physiologically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Salts can also be used in these compositions, for example, mineral salts such as hydrochlorides, hydrobromides, phosphates, or sulfates, as well as salts of organic acids such as acetates, proprionates, malonates, or benzoates. A composition of the invention typically contains a liquid, such as water, saline, glycerol, and ethanol, as well as substances such as wetting agents, emulsifying agents, or pH buffering agents, and is typically prepared as an injectable, as a suspension of viral display packages in a liquid medium. Such compositions permit preparation of screening kits.

The above disclosure generally describes the present invention, and all documents cited in this disclosure are expressly incorporated by reference herein a more complete understanding can be obtained by reference to the following specific examples, which are provided for purposes of illustration only and are not intended to limit the scope of the invention.

EXAMPLE 1

This example demonstrates screening of test substances from a small molecule library for the ability to inhibit human matrix type-I metalloprotease (MT-1 MMP/MMP14).

Viral display packages comprising a β-galactosidase gene and displaying a recombinant viral envelope protein are constructed as follows. A construct encoding (1) the N-terminal 208 amino acids of a 4070A viral envelope protein, (2) Pro-Leu-Gly-Leu-Trp-Ala, which is a protease cleavage site for human MT1-MMP, (3) a Moloney murine leukemia virus envelope protein and (4) a phleomycin resistance gene is transfected into TELCeB6 cells by calcium phosphate precipitation (Sambrook et al., 1989). These cells produce viral display packages which carry a β-galactosidase gene. Stably transfected cells are selected with 50 μg/ml phleomycin. Supernatant containing viral display packages is harvested from pools of confluent phleomycin-resistant clones after overnight incubation in DMEM and 10% FBS.

HT1080 cells (ATCC Accession No. CCL-121), which display Pit-2/Ram-1 receptors on their cell surface and express MT1-MMP, are dispensed into 96-well plates. Following overnight incubation at 37° C. with culture medium, one test substance from a small molecule library is added to each well in the plates, leaving some wells without any added test substances to serve as negative controls. Either a single concentration (e.g. 10 μM) of each test substance or several concentrations, ranging from 1 nM to 100 mM, are added to separate wells.

After incubation for at least 1 hour with the test substances, supernatant from the viral display package producer cells is filtered through a 0.45 μm filter and added to each well together with 8 μg/ml polybrene. After incubating the viral display packages and the target cells for 3–5 hours at 37° C., supernatant is removed and the cells are incubated with regular medium for 24–48 hours.

The substrate O-nitrophenyl- -D-galactopyranoside (ONPG) is then added to each well. The absorbance of each well is read at 405 nm in a spectrophotometer plate reader. Optical densities above a threshold level determined by the absorbance of the contents of the negative control wells are recorded and traced to the test substance that produced the effect a test substance that increases the optical density of the contents of a test well by at least 10% over the optical density of the contents of the negative control wells, or which increases the number of test wells with an optical density over the threshold level by at least two-fold, is identified as a potential protease inhibitor drug.

EXAMPLE 2

This example demonstrates screening of test substances from a small molecule library for the ability to inhibit factor Xa protease.

Viral display packages comprising a β-galactosidase gene and displaying a recombinant viral envelope protein are constructed as follows a construct encoding (1) the N-terminal 208 amino acids of of a 4070A viral envelope protein, (2) Ile-Glu-Gly-Arg, which is a protease cleavage site for factor Xa protease, (3) the envelope protein of Moloney murine leukemia virus and (4) a phleomycin resistance gene is transfected into TELCeB6 cells using Superfect (QIAGEN). Stably transfected cells are selected with phleomycin at 50 μg/ml. Supernatant containing viral display packages is harvested from pools of confluent clones after overnight incubation in DMEM and 10% FBS. TE671 cells (ATCC Accession No. CRL-8805) displaying Pit-2/Ram-1 receptors are dispensed into 96-well plates. Following overnight incubation at 37° C. with culture medium, one test substance from a small molecule library is added to each well in the plates, leaving some wells without any added test substances to serve as negative controls. Several concentrations of each test substance are added to separate wells, ranging from 1 nM to 1 mM. Recombinant factor Xa protease (New England Biolabs) is then added to each well to give a final concentration of 4 ug/ml.

Supernatant from the viral display package producer cells is then filtered through a 0.45 μm filter and added to each well together with 8 μg/ml polybrene. After incubating the viral display packages and the target cells for 3–5 hours at 37° C., supernatant is removed and the cells are incubated with regular medium for 48–72 hours.

The substrate O-nitrophenyl- -D-galactopyranoside (ONPG) is then added to each well. The absorbance of each well is read at 405 nm in a spectrophotometer plate reader. Optical densities above a threshold level determined by the absorbance of the contents of the negative control wells are recorded and traced to the test substance that produced the effect. A test substance that increases the optical density of the contents of a test well by at least 10% over the optical density of the contents of the negative control wells, or which increases the number of test wells with an optical density over the threshold level by at least two-fold, is identified as a potential protease inhibitor drug.

What is claimed is:

1. A method of identifying a test substance for the ability to inhibit a protease, comprising the steps of:

contacting a target cell comprising a protease with a viral display package in the presence of a test substance, wherein the viral display package comprises (a) a transferable label and (b) a recombinant viral envelope protein comprising in sequential order (i) a receptor-binding polypeptide which binds to a receptor on the surface of the target cell, (ii) a protease cleavage site for said protease expressed by the target cell, and (iii) a fusion-mediating polypeptide, such that proteolytic cleavage of said cleavage site does not permit substantial transfer of the transferable label from the viral display package to the target cell; and detecting the transferable label, if any, in the target cell, wherein detection of transferable label or a greater amount of transferable label in the target cell in the presence of the test substance relative to the absence of the test substance identifies the test substance as an inhibitor of said protease.

2. The method of claim 1 wherein the receptor-binding polypeptide is a first viral envelope protein, or a receptor binding domain thereof.

3. The method of claim 2 wherein the first viral envelope protein is selected from the group consisting of a 4070A envelope protein and a Moloney murine leukemia virus envelope protein.

4. The method of claim 1 wherein the fusion-mediating polypeptide is a substantially intact viral envelope protein.

5. The method of claim 1 wherein the fusion-mediating polypeptide is a fusion-mediating polypeptide of a second viral envelope protein, wherein the first and second viral envelope proteins are derived from different viruses.

6. The method of claim 2 wherein the fusion-mediating polypeptide is a fusion-mediating polypeptide of a second viral envelope protein.

7. The method of claim 6 wherein the first and second viral envelope proteins are obtained from the same virus.

8. The method of claim 7 wherein the virus is a murine leukemia retrovirus.

9. The method of claim 8 wherein the murine leukemia virus is selected from the group consisting of a Moloney murine leukemia virus and a 4070A murine leukemia virus.

10. The method of claim 1 wherein the target cell is a eukaryotic cell.

11. The method of claim 10 wherein the target cell is a mammalian cell.

12. The method of claim 11 wherein the target cell is a human cell.

13. The method of claim 1 wherein the transferable label is a reporter gene which encodes a detectable product.

14. The method of claim 1 wherein the transferable label is a gene encoding a selectable marker.

15. The method of claim 1 wherein the protease cleavage site is contained within an amino acid linker sequence.

16. A method of identifying a test substance for the ability to inhibit a protease, comprising the steps of:

contacting a plurality of target cells, members of which comprise a protease with a plurality of viral display package members in the presence of a test substance, wherein each said member of the plurality of viral display package members comprises (a) a transferable label and (b) a recombinant viral envelope protein comprising in sequential order (I) a receptor-binding polypeptide which binds to a receptor on the surface of the target cell, (ii) a protease cleavage site for said protease expressed by members of the plurality of target cells, and (iii) a fusion-mediating polypeptide, such that proteolytic cleavage of said cleavage site does not permit substantial transfer of the transferable label from said members of the plurality of viral display packages to said members of the plurality of target cells; and detecting the transferable label, if any, in said members of the plurality of target cells, wherein detection of transferable label in a number of target cells or a greater number of target cells in the presence of the test substance relative to the absence of the test substance identifies the test substance as an inhibitor of said protease.

17. The method of claim 16 wherein the receptor-binding polypeptide is a receptor-binding polypeptide of a first viral envelope protein.

18. The method of claim 17 wherein the first viral envelope protein is selected from the group consisting of a 4070A envelope protein and a Moloney murine leukemia virus envelope protein.

19. The method of claim 16 wherein the fusion-mediating polypeptide is a substantially intact viral envelope protein.

20. The method of claim 16 wherein the fusion-mediating polypeptide is a fusion-mediating polypeptide of a second viral envelope protein.

21. The method of claim 17 wherein the fusion-mediating polypeptide is a fusion-mediating polypeptide of a second viral envelope protein, wherein the first and second viral envelope proteins are derived from different viruses.

22. The method of claim 21 wherein the first and second viral envelope proteins are obtained from the same virus.

23. The method of claim 22 wherein the virus is a murine leukemia retrovirus.

24. The method of claim 23 wherein the murine leukemia virus is selected from the group consisting of a Moloney murine leukemia virus and a 4070A murine leukemia virus.

25. The method of claim 16 wherein the target cell is a eukaryotic cell.

26. The method of claim 25 wherein the target cell is a mammalian cell.

27. The method of claim 26 wherein the target cell is a human cell.

28. The method of claim 16 wherein the transferable label is a reporter gene which encodes a detectable product.

29. The method of claim 16 wherein the transferable label is a gene encoding a selectable marker.

30. A method of delivering a transferable label to a target cell, comprising the step of:

contacting a target cell comprising a protease with a viral display package and a protease inhibitor, wherein the viral display package comprises (a) a transferable label and (b) a recombinant viral envelope protein comprising in sequential order (I) a receptor-binding polypeptide which binds to an amphotropic receptor on the surface of the target cell, (ii) a protease cleavage site for said protease, and (iii) a fusion-mediating polypeptide which binds to an ecotropic receptor on the surface of the target cell, such that transfer of said transferable label from the viral display package to the target cell is dependent upon inhibition of said protease, whereby a greater amount of transferable label is transferred to the target cell in the presence of said protease inhibitor relative to the absence of said protease inhibitor.

31. The method of claim 30 wherein the receptor-binding polypeptide is a receptor-binding domain of an amphotropic virus envelope protein.

32. The method of claim 31 wherein the amphotropic envelope protein is a 4070A murine leukemia virus envelope protein.

33. The method of claim 30 wherein the fusion-mediating polypeptide is a fusion-mediating domain of an ecotropic virus envelope protein.

34. The method of claim 33 wherein the ecotropic virus envelope protein is a Moloney murine leukemia virus envelope protein.

35. The method of claim 30 wherein the recombinant viral envelope protein comprises a receptor-binding domain of an amphotropic envelope protein and a fusion-mediating domain of an ecotropic virus envelope protein.

36. The method of claim 35 wherein the amphotropic envelope protein is a 4070A virus envelope protein and wherein the ecotropic virus envelope protein is a Moloney murine leukemia virus envelope protein.

37. The method of claim 36 wherein the target cell is a mammalian cell.

38. The method of claim 37 wherein the mammalian cell is a human cell.

39. The method of claim 38 wherein the mammalian cell is in a mammalian body.

40. The method of claim 38 wherein the human cell is in a human body.

41. The method of claim 30 wherein the target cell is in vitro.

42. The method of claim 30 wherein the transferable label is an expressible polynucleotide.

43. A method of delivering a transferable label to a target cell, comprising the step of:

contacting a plurality of target cells, members of which comprise a protease with a plurality of viral display package members and a protease inhibitor, wherein each said member of the plurality of viral display package members comprises (a) a transferable label and (b) a recombinant viral envelope protein comprising in sequential order (I) a receptor-binding polypeptide which binds to an amphotropic receptor on the surface of the target cell, (ii) a protease cleavage site for said protease and (iii) a fusion-mediating polypeptide which binds to an ecotropic receptor on the surface of the target cell, such that transfer of said transferable label from said members of the plurality of viral display packages to said members of the plurality of target cells is dependent upon inhibition of proteolytic cleavage of said cleavage site, whereby the transferable label is transferred to a number of or a greater number of target cells in the presence of said protease inhibitor relative to the absence of said protease inhibitor.

44. The method of claim 43 wherein the receptor-binding polypeptide is a receptor-binding domain of an amphotropic virus envelope protein.

45. The method of claim 44 wherein the amphotropic envelope protein is a 4070A murine leukemia virus envelope protein.

46. The method of claim 43 wherein the fusion-mediating polypeptide is a fusion-mediating domain of an ecotropic virus envelope protein.

47. The method of claim 46 wherein the ecotropic virus envelope protein is a Moloney murine leukemia virus envelope protein.

48. The method of claim 43 wherein the recombinant viral envelope protein comprises a receptor-binding domain of an amphotropic envelope protein and a fusion-mediating domain of an ecotropic virus envelope protein.

49. The method of claim 48 wherein the amphotropic envelope protein is a 4070A virus envelope protein and wherein the ecotropic virus envelope protein is a Moloney murine leukemia virus envelope protein.

50. The method of claim 43 wherein the target cell is a mammalian cell.

51. The method of claim 50 wherein the mammalian cell is a human cell.

52. The method of claim 50 wherein the mammalian cell is in a mammalian body.

53. The method of claim 51 wherein the human cell is in a human body.

54. The method of claim 43 wherein the target cell is in vitro.

55. The method of claim 43 wherein the transferable label is an expressible polynucleotide.

* * * * *